(12) United States Patent
Van Berkel (10) Patent No.: US 6,803,566 B2
(45) Date of Patent: Oct. 12, 2004

(54) SAMPLING PROBE FOR MICROARRAY READ OUT USING ELECTROSPRAY MASS SPECTROMETRY

(75) Inventor: Gary J. Van Berkel, Clinton, TN (US)

(73) Assignee: UT-Battelle, LLC, Oak Ridge, TN (US)

(*) Notice: Subject to any disclaimer, the term of this patent is extended or adjusted under 35 U.S.C. 154(b) by 21 days.

(21) Appl. No.: 10/123,629

(22) Filed: Apr. 16, 2002

(65) Prior Publication Data

US 2003/0193020 A1 Oct. 16, 2003

(51) Int. Cl.$^7$ ............................. B01D 59/44; H01J 49/00
(52) U.S. Cl. ....................... 250/288; 250/281; 250/282
(58) Field of Search ............................... 250/281, 282, 250/288, 423 R (56) References Cited

U.S. PATENT DOCUMENTS

| | | | | |
|---|---|---|---|---|
| 4,994,165 A | * | 2/1991 | Lee et al. | 204/453 |
| 5,015,845 A | * | 5/1991 | Allen et al. | 250/288 |
| 5,245,185 A | * | 9/1993 | Busch et al. | 250/288 |
| 6,066,848 A | | 5/2000 | Kassel et al. | |
| 6,225,047 B1 | | 5/2001 | Hutchens et al. | |
| 6,478,238 B1 | * | 11/2002 | Wachs et al. | 239/338 |
| 2002/0000517 A1 | | 1/2002 | Corso et al. | |
| 2002/0011562 A1 | | 1/2002 | Park | |

OTHER PUBLICATIONS

Mann, M., et al., "Error–Tolerant Identification of Peptides in Sequence Databases by Peptide Sequence Tags" Analytical Chemistry, vol. 66, No. 24, Dec. 15, 1994, pp. 4390–4399.

Cargile, B.J., et al., "Identification of Bacteriophage MS2 Coat Protein from E. coli Lysates via Ion Trap Collisional Activation of Intact Protein Ions", Analytical Chemistry, vol. 73, No. 6, Mar. 15, 2001, pp. 1277–1285.
Schultz, G.A., et al., "A Fully Integrated Monolithic Microchip Electrospray Device for Mass Spectrometry", Analytical Chemistry, vol. 72, No. 17, Sep. 1, 2000, pp. 4058–4063.
Felten, C., et al. "Automated High–Throughput Infusion ESI–MS with Direct Coupling to a Microtiter Plate", Analytical Chemistry, vol. 73, No. 7, Apr. 1, 2001, pp. 1449–1454.
Wachs, T., et al., "Electrospray Device for Coupling Microscale Separations and Other Miniaturized Devices with Electrospray Mass Spectrometry", Analytical Chemistry, vol. 73, No. 3, Feb. 1, 2001, pp. 632–638.
Zhang, B. et al., "High–Throughput Microfabricated CE/ESI–MS: Automated Sampling from a Microwell Plate", Analytical Chemistry, vol. 73, No. 11, Jun. 1, 2001, pp. 2675–2681.

* cited by examiner

Primary Examiner—John R. Lee
Assistant Examiner—Paul M. Gurzo
(74) Attorney, Agent, or Firm—Akerman Senterfitt (57) ABSTRACT

An automated electrospray based sampling system and method for analysis obtains samples from surface array spots having analytes. The system includes at least one probe, the probe including an inlet for flowing at least one eluting solvent to respective ones of a plurality of spots and an outlet for directing the analyte away from the spots. An automatic positioning system is provided for translating the probe relative to the spots to permit sampling of any spot. An electrospray ion source having an input fluidically connected to the probe receives the analyte and generates ions from the analyte. The ion source provides the generated ions to a structure for analysis to identify the analyte, preferably being a mass spectrometer. The probe can be a surface contact probe, where the probe forms an enclosing seal along the periphery of the array spot surface.

28 Claims, 5 Drawing Sheets

SAMPLING PROBE FOR MICROARRAY READ OUT USING ELECTROSPRAY MASS SPECTROMETRY

STATEMENT REGARDING FEDERALLY SPONSORED RESEARCH OR DEVELOPMENT

The United States Government has rights in this invention pursuant to Contract No. DE-AC05-00OR22725 between the United States Department of Energy and UT-Battelle, LLC.

FIELD OF THE INVENTION

This invention relates generally to methods and apparatus for transport, ionization and subsequent analysis of analytes, and more specifically to methods and apparatus for analyzing a plurality of sample spots on an array using electrospray mass spectrometry.

BACKGROUND OF THE INVENTION

The study of protein complements of cells, tissues or whole organisms is referred to as proteomics. Proteomics is of great interest and much progress has been made in recent years in large part because of new enabling analytical technologies. One theme in proteomics is to monitor the expression of proteins in a biological system as the system responds to a stimulus. Currently, two-dimensional gel electrophoresis (2-DE) is the most common and powerful platform for the measurement of such protein complements. This approach can support expression profiling of several thousand proteins in multiple samples.

However, 2-DE has several significant limitations. These limitations include, for example, difficulty in running membrane proteins, complicated gel image analysis and manual preparation and running of the gels. Moreover, 2-DE requires spot excising and clean-up to utilize the highly specific and sensitive mass spectrometric-based protein identification methods employed. Therefore, alternative measurement platforms for protein expression profiling within complex samples are being explored.

Protein "arrays" or "chips" are one potential alternative. In addition to protein expression profiling, this technology has potential uses in identifying protein-protein interactions, protein substrates or potential candidates in drug discovery processes. This approach to screening protein activity benefits from the same advantages as commercially available DNA microarrays for mRNA expression analysis, namely high-throughput parallel, quantitative microscale analysis. It also has advantages over DNA microarrays.

True expression analyses must be done at the protein level because the final active product of most genes is the protein and protein expression and mRNA expression are not necessarily quantitatively linked. Furthermore, proteins can be synthesized in both active and inactive forms. To understand the biological function of a gene, the amount of active gene product must generally be determined.

Analysis of nucleic acid chips is usually performed using a fluorescent probe reporter attached to the analyte. A number of problems are associated with using this approach for protein array read out. First, and foremost, the fluorescence approach requires that only the analytes bind to the capture molecule and that non-specific binding is minimal. This is usually not the case with proteins, especially when the binding conditions cannot be optimized for each specific interaction. A second problem is that labeling of the proteins with a fluorescent probe can change their binding characteristics and can destroy protein complexes that exist in solution. Finally, the fluorescence approach cannot distinguish among the different forms of a given protein. This includes situations wherein the active and inactive form of the protein are captured and give equivalent signals. Both of these problems plague the current parallel standard for protein detection and quantitation, enzyme linked immunosorbant assay (ELISA), which operates on a capture/detection format.

Mass spectrometry (MS) techniques offer advantages for both detecting and identifying proteins. At present there is no other technology that can rival the combination of speed of analysis, sensitivity, and high accuracy measurement of molecular mass afforded by mass spectrometry in protein analysis. High-resolution, accurate mass determination allows detection of post-translational modification of proteins, even in protein mixtures, which is difficult to assess by other available techniques. Peptide fragments of proteins generated enzymatically, and analyzed by mass spectrometry, are now routinely used to identify the whole molecule via on-line protein database searching (peptide mapping).

Alternatively, new methods allow protein identification from the fragments generated from intact proteins in the gas-phase using tandem mass spectrometry, eliminating the need for enzymatic digestions. Tandem mass spectrometry uses two stages of mass analysis, one to preselect an ion and the second to analyze fragments induced, for instance, by collision with an inert gas, such as argon or helium. This dual analysis can be tandem in time, or more commonly tandem in space. Tandem in space is implemented using two mass spectrometers in series.

Mass spectrometry is now regarded as having great potential as a method for protein microarray read out. There are currently two ionization methods commonly used to generate gas-phase ions from proteins for analysis by mass spectrometry. These methods are matrix-assisted laser desorption ionization (MALDI) and electrospray (ES) ionization. Of these two methods, the most common choice for protein array read out is MALDI-MS, which is a surface analysis technique.

MALDI-MS approaches to protein chip read out are currently being exploited by two different companies, Ciphergen Biosystems, Inc. (Fremont, Calif.) and Intrinsic Bioprobes, Inc. (Tucson, Ariz.). They each offer protein chips for MALDI-MS containing from four to eight interaction sites. These commercial products can be obtained with particular general affinities for protein capture built-in, e.g., hydrophobic or hydrophilic interaction, anion exchange, cation exchange, and immobilized metal affinity substrates for capturing metal binding proteins. Alternatively, special order chips can be obtained with immobilized receptor species of the investigator's choice. For example, the immobilized substrates can be a specific antibody. While the commercial products are not true arrays, there have been laboratory demonstrations of the preparation and MALDI-MS analysis of protein interaction arrays as large as ten by ten (100 spots).

The commercial availability of MALDI-MS protein chip products is an indication of their utility. Nonetheless, the use of MALDI-MS for chip read out presents significant analytical limitations. There is a low number density of analyte at any small point on a particular array spot where the laser beam interacts to generate ions. This negatively impacts detection levels. Detection levels in MALDI-MS precipitously decline above a molecular mass of about 15 kDa. This can severely limit the range of proteins that can be analyzed directly. Time consuming enzymatic digestion methods are also needed for generating low mass peptides that are more amenable to detection when larger proteins are analyzed. These digestions are also needed to generate peptides for protein identification by peptide mapping. Mass accuracies in MALDI-MS are usually no better than about 0.01% (e.g., +6 Da for bovine albumin, ca. 66,000 Da). Finally, analysis of the arrays requires removal of the analyte from the native liquid environment within which the interactions occur and the application of a chemical matrix to facilitate desorption and ionization, followed by a drying step.

Electrospray is an alternative to MALDI. Electrospray generally involves flowing a sample liquid into an electrospray ion source comprising a small tube or capillary which is maintained at a high voltage, in absolute value terms, with respect to a nearby surface. The nearby (e.g. 1 cm) surface is commonly referred to as the counter electrode. Conventional ES systems for mass spectrometry apply high voltage (relative to a ground reference) to the emitter electrode while holding the counter electrode at a lower, near ground reference voltage. For the positive ion mode of operation, the voltage on the emitter is high positive, while for negative ion mode the emitter voltage is high negative.

The liquid introduced into the tube or capillary is dispersed and emitted as fine electrically charged droplets (plume) by the applied electrical field generated between the tube or capillary which is held at high voltage, referred to as the working electrode, and the nearby surface.

The ionization mechanism generally involves the desorption at atmospheric pressure of ions from the fine electrically charged particles. The ions created by the electrospray process can then be used for a variety of applications, such as mass analyzed in a mass spectrometer.

In a typical ES-MS process, a solution containing analytes of interest is directed to the ES emitter which is held at high voltage, resulting in a charged solvent droplet spray or plume. The droplets drift towards the counter electrode under the influence of the electric field. As the droplets travel, gas-phase ions are liberated from the droplets. This process produces a quasi-continuous steady-state current with the charged droplets and ions constituting the current and completing the series circuit.

Although ES-MS is known, the use of ES-MS for automatically reading out a plurality of spots, such as from a protein chip array, has not been demonstrated. This is likely because of the technical challenges of sampling analytes from small spots on a sample surface with a liquid flow system in an automated way. Specifically, electrospray normally operates by having a sample dissolved in solution flow through transfer tubing to the ion source of the mass spectrometer. When trying to analyze a surface with electrospray a significant challenge is presented in producing a probe suitable for transporting a normally solid-state surface sample into solution and then into the transfer line. In addition, a sophisticated structure is needed to control the alignment of the probe with the surface, the structure generally providing fine resolution of the probe movement relative to the surface.

SUMMARY OF THE INVENTION

A method for identifying analytes disposed on or in surface arrays includes the step of providing a surface array including at least one spot. The spot holds at least one analyte. At least one eluting solvent is flowed across the spot. The solvent directs at least a portion of the analyte away from the spot. At least a portion of the analyte is ionized into a plurality of ion fragments using an electrospray ion source. The plurality of ion fragments are then analyzed permitting identification of the analyte. The analytes can include intact proteins, protein fragments, pharmaceutical agents and antibodies.

The method can include the step of automatically stepping to at least one of the other spots and repeating the flowing, ionizing and analyzing steps. As used herein, the term "stepping" is used synonymously with the term scanning and refers to movement from one array spot to another array spot.

The analyzing step can include mass spectrometry. Mass spectrometry can be tandem mass spectrometry.

The flowing step can include the step of flowing a wash solvent before flowing the eluting solvent. The method can also include the step of flowing at least one reagent to the spot before flowing the eluting solvent.

The probe can be a multi-axial liquid junction probe, the liquid junction probe contacting the spot using a liquid bridge. The probe can be a multi-axial surface contact probe, the surface contact probe adapted for forming a sealed enclosure around the periphery of the spot. The surface contact probe can include an o-ring seal for forming the sealed enclosure. The surface contact probe can use positive pressure for the flowing step, wherein the eluting solvent and the analyte are transmitted through the probe under influence of the applied positive pressure.

In the embodiment which includes automatic stepping, the positioning device can provide x, y and z positional control about a substantially flat surface with at least 1 nm resolution for each dimension. The positioning device can be a piezoelectric positioner and controller of a scanning probe electrochemical microscope (SECM).

The method is adapted to sample spot areas of less than about 0.04 mm$^2$. The surface array can be a protein array, thin-layer chromatography plates, SDS polyacrylamide gel electrophoresis (SDS-PAGE), isoelectric focusing gels or solid phase extraction materials.

An automated sampling system is for obtaining samples from surface arrays having a plurality of spots for analysis. The spots have at least one analyte disposed on or contained within. The system includes at least one probe. The probe includes an inlet for flowing at least one eluting solvent to the spots and further includes an outlet for directing the analyte away from the spot. An automatic positioning system is provided for translating the probe relative to the spots to permit sampling of any of the spots.

An electrospray ion source having an input fluidicly connected to the probe is provided for receiving the analyte and generating ions from the analyte. The system includes a structure for analysis of the generated ions, the structure for analysis receiving the ions for the electrospray ion source. The structure for analysis can include a mass spectrometer or a tandem mass spectrometer.

The probe can be a multi-axial liquid junction probe, the liquid junction probe contacting the spots using a liquid bridge. The probe can also be multi-axial surface contact probe, the surface contact probe adapted for forming a sealed enclosure around a periphery of the spots.

The automatic positioning system can provide the ability to step from spot to spot. For example, a piezoelectric positioner and controller of a scanning probe electrochemical microscope (SECM) can be used for this purpose.

BRIEF DESCRIPTION OF THE DRAWINGS

A fuller understanding of the present invention and the features and benefits thereof will be accomplished upon review of the following detailed description together with the accompanying drawings, in which.

DETAILED DESCRIPTION OF THE PREFERRED EMBODIMENTS

A system for detecting at least one analyte disposed in any of a plurality of spots in a surface array includes at least one sampling probe. An automatic positioning device is preferably provided for aligning the sampling probe relative to the array spots and for stepping to other array spots so that the detection process can be automatically repeated. The probe includes an inlet for flowing at least one eluting solvent to any of the array spots to carry the analyte and an outlet for directing the analyte away from the spot to an electrospray ion source for ionizing the analyte. A structure for analyzing ions, preferably being a mass spectrometer, identifies the analyte by analysis of the ions generated by the ES source. Accordingly, the invention does not require complicated and often unreliable extrinsic labeling methods for analysis generally required by previous methods for array sampling.

The invention may be used to sample virtually any surface of interest. Accordingly, the invention has a broad range of potential applications. Protein microarrays is one such application. Protein microarray technology is a rapidly expanding market with a rapid projected growth rate. Some general uses of the invention include protein purification, protein expression profiling and protein interaction profiling, including protein-protein interactions and drug discovery. A road block to growth in this area has been identification of sensitive molecular specific detection methods for arrays that do not required complicated and often unreliable extrinsic labeling methods. Significantly, the invention does not require labeling for analyte detection.

With regard to protein arrays, substrate surfaces can be coated with one or more regions having immobilized capture material thereon. For example, protein arrays can contain antibodies covalently immobilized onto the array surface to capture corresponding antigens from a complex mixture. Different spots can have different capture material thereon. Many different types of capture material substances can be bound to array substrates including antibodies, receptors, ligands, nucleic acids (e.g. DNA), carbohydrates, gels (e.g. isolectric focusing gels), and chromatographic surfaces, such as cationic, anionic, hydrophobic, hydrophilic surfaces. Molecular imprinted materials may also be used as a capture material. Some surfaces can be designed to have broad specificity and bind whole classes of proteins, while others can be designed to be highly specific and bind to one or only a few proteins from a complex sample.

After the capture step, the analyte is bound to the capture material and disposed on the array. The array is then preferably washed with a suitable wash solvent to reduce nonspecific binding. Rather than using a drying step followed by short bursts of high power laser light to uncouple the retained proteins from a portion of the array surface as in MALDI, the invention uses one or more solvents to uncouple retained proteins, or other bound analytes generally from the entire spot area, without the need for application of a matrix and the associated drying step. Analyte is then ionized using electrospray ionization and the generated ions analyzed using any suitable analysis technique, such as mass spectrometry. Although mass spectrometry is generally preferred, ion mobility or a combination of ion mobility and mass spectrometry could be used. Light scattering detectors may also be used for analysis, such as the DUSTRAK model 8520 (ITI-044), provided by TSI Incorporated, St. Paul, Minn.

Figure 1:
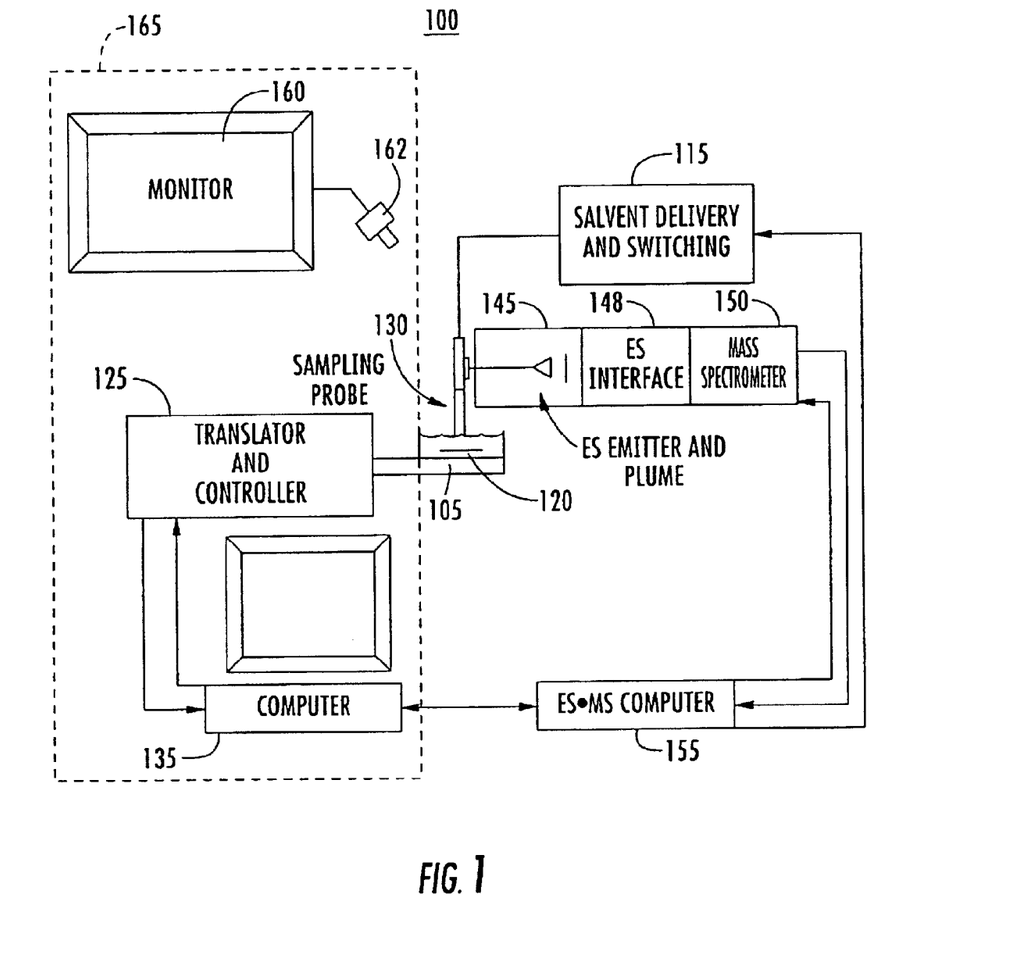
FIG. 1 illustrates a sampling probe/ES-MS for surface array read out, according to an embodiment of the invention.

FIG. 1 shows an ES-MS sampling system 100 for surface array read out, according to an embodiment of the invention. Surface array 120 is disposed on a substrate (not shown), the substrate disposed on a stage 105. Surface array 120 includes a plurality of discrete array interaction spots (not shown). Each spot has an area generally being less than about 1 mm$^2$. System 100 is adapted to sample spot areas as small as about 0.04 mm$^2$, more preferably, sample spot areas as small as about 0.01 mm$^2$.

Array 120 is preferably a protein array having capture material disposed thereon, but can be any surface array, such as thin-layer chromatography plates, SDS polyacrylamide gel electrophoresis (SDS-PAGE), isoelectric focusing gels and solid phase extraction materials. For example, spots can include one or more regions having immobilized capture material thereon, such as nucleic acids or antibodies.

The array substrate (not shown) is typically an inert, non-porous material. For example, glass, a surface layer of SiO$_2$ disposed on a material such as silicon, various plastics or alumina may generally be used as substrate materials.

Although the system 100 is shown as having one sampling probe 130 and will be described as generally being a serial readout system, the system can be configured as a parallel, multiplexed system. A multiplexed probe system can increase sample throughput. For example, commercially available ES systems provide up to 8 indexed sprayers. Each sprayer can operate in parallel by rapidly sampling the sample stream from each sprayer in a cyclical fashion. Assuming a single mass spectrometry analysis system is used, the amount of time the spray from any one emitter is sampled is reduced by a multiple of the reciprocal of the number of sprayers.

In an alternate embodiment, discrete array positions of the surface array 120 can be provided with their own dedicated sprayers. This may be possible with soon to be commercialized microfabricated arrays of ES nozzles, providing faster, fully automated serial read out of surface arrays.

A translator and controller 125, preferably being a piezoelectric based translator and controller integrated into a scanning electrochemical microscope (SECM) 165, is provided for aligning the sampling probe 130 relative to any of the array spots included on array 120 and stepping between individual spots. A SECM 165 is a type of scanned probe microscope (SPM) related to scanning tunneling and atomic force microscopes. SPMs operate by scanning or "rastering" a small probe tip over the surface to be imaged. In SECM, imaging occurs in an electrolyte solution with an electrochemically active tip.

SECM systems are commercially available for providing reproducible x, y and z positional control about a substantially flat surface with better than 1 nm resolution and an x and y travel distance of 5 cm. Systems are provided by CH Instruments, Inc., Austin, Tex. This positional resolution and travel distance are sufficient for virtually all currently used surface devices and allows precise and complete sampling of large densely packed surface arrays with interaction locations with linear dimensions as small as about 100 $\mu$m in size. Another positioning device of similar specifications could be used in place of the SECM.

SECM 165 preferably includes a video microscope 162 and video monitor 160, piezo based translator and controller 125 and SECM computer 135. SECM computer 135 supervises the interaction between sampling probe 130 and chip array 120 to spatially position the sampling probe 130 relative to the array surface to obtain and deliver captured material to ES ion source 145. Sampling probe 130 can be moved relative to chip array 120, or chip array 120 can be moved relative to sampling probe 130 to provide contact between the same.

A solvent delivery system 115 is adapted to provide fluids including eluting solvents. A pressure differential propels the fluids. In one embodiment positive pressure can be used to propel the fluids. However, a vacuum applied to the output can also generally be used in the absence of positive pressure. As used herein, the term "positive pressure" refers to a pressure above atmospheric pressure necessary to deliver the fluids through the system at the desired flow rate.

A syringe pump, gas pressure or other pumping systems may be used. As noted above, a vacuum may also be used. In one embodiment using a vacuum, flow caused by pressure can be matched to draw the liquid out by a venturi vacuum effect.

Fluids are delivered by delivery system 115 through a suitable fluid conduit to an inlet of sampling probe 130 which directs the eluting solvent to surface array spots to uncouple captured analyte. Analyte together with the eluting solvent is then directed by sampling probe 130 to an outlet of the probe and away from the spot to an electrospray ion source for ionizing the analyte.

Although the substrate (not shown) is typically formed from non-porous material, the array substrate can be formed from porous materials such that the position of each interaction spot is on a porous medium. Thus, if the surface where the spot was placed is substantially porous, solvent can be alternatively pushed through the array by solvent delivery system 115 to transfer analyte into a suitable probe.

ES ion source 145 produces and supplies ions derived from analyte supplied by sampling probe 130 to mass spectrometer 150. Mass spectrometer includes electrospray interface 148. The mass spectrometer 150 is preferably selected based on required performance figures-of-merit, such as scan speed, mass accuracy, ion/ion chemistry for the particular intended use. Mass spectrometer 150 is preferably a tandem mass spectrometer.

The ES ion source 145 and mass spectrometer 150 are preferably computer controlled, such as by ES-MS computer 155. ES-MS computer 155 can be separate from SECM computer 135 or integrated with the same.

ES-MS sampling using the invention provides several significant advantages as compared to MALDI-MS. ES-MS introduces the sample to the mass spectrometer 150 in a liquid solution, and therefore, the possibility exists for sampling the components interacting at each point on an array while the surface array 120 remains in a liquid environment. In MALDI-MS, analysis of array spots requires the removal from the native liquid environment within which the interactions occur, the application of a chemical matrix to facilitate desorption and ionization, followed by a drying step.

Using the invention, all the material on the interaction spot can potentially be collected and directed to the mass spectrometer 150, not just the small fraction that interacts with the laser beam in MALDI-MS. Moreover, ES-MS does not have the same drop off in detection level as does MALDI-MS as molecular mass increases. Furthermore, up to a mass of about 60 kDa, even modest mass analyzers with nominal mass resolution can obtain mass accuracies as good or better than +0.002% (e.g., +1.3 Da for bovine albumin). Even better mass determinations can be provided by selection of higher performance mass analyzers, such as an ES equipped orthogonal ion injection time-of-flight (O-TOF) or Fourier Transform Mass Spectrometer (FTMS).

Thus, using the invention, proteins can be identified in two basic ways. The first case is on the basis of high accuracy molecular mass determinations which can be performed even when mixtures of proteins are present. Suitable instruments include the FTMS and O-TOF. Ion/ion chemistry and instrumentation can also be used to analyze relatively complicated protein mixtures. Mixture analysis is regarded as an advantage of the MALDI-MS method. In the second case, proteins are identified on the basis of sequence tags generated from tandem mass spectrometry of the whole protein. FTMS, O-TOF, or ion/ion instrumentation might be used to generate the sequence tags. This "top-down" approach to protein identification eliminates the need for the time consuming enzymatic digestion methods necessary for protein identification with chip read out by MALDI-MS.

Sampling probe 130, which transfers the uncoupled captured analyte (e.g. protein) from the surface array surface for identification, is preferably a miniature multi-conduit probe, such as a coaxial capillary probe. The probe includes at least one fluid conduit for receiving fluid flow of an eluting solvent or other fluids. At least one other fluid conduit provides fluid output from probe 130, the fluid output including the analyte and one or more other fluids. When positive pressure is use to drive fluids, the typical positive pressure ranges depend on the flow rate and the tube diameter and length. However, a few psi would generally be a minimum and 2000–3000 psi would generally be a maximum.

Figure 2A:
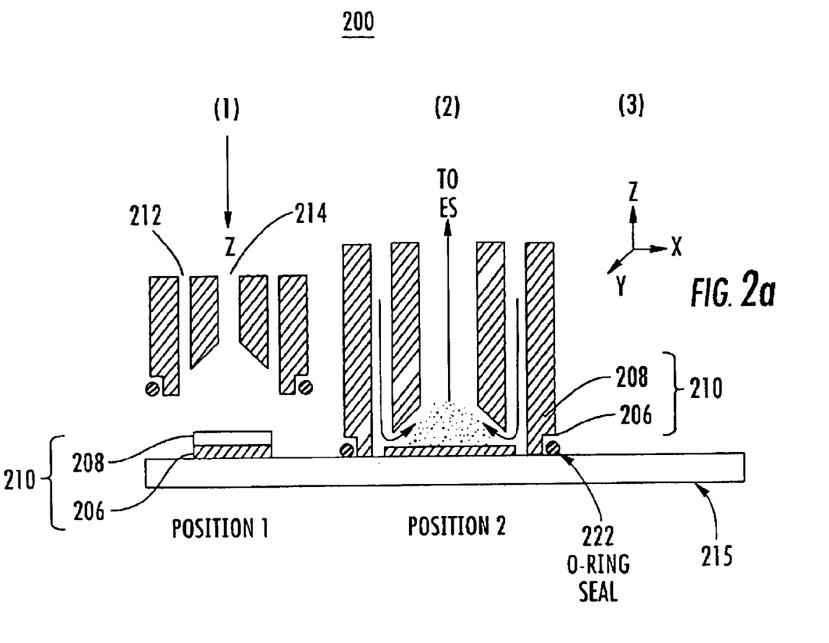
FIG. 2(a) illustrates a surface contact probe, according to an embodiment of the invention.
Figure 2B:
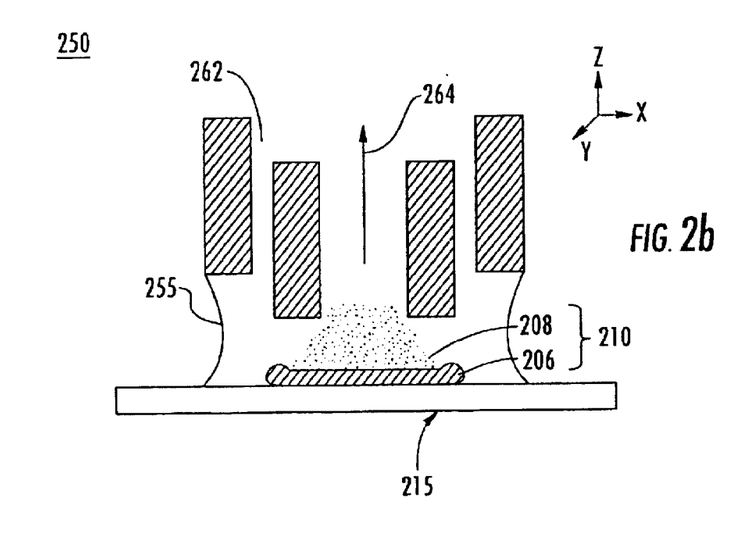
FIG. 2(b) illustrates a liquid junction probe, according to an embodiment of the invention.

Two basic types of sampling probe designs adapted for ES-MS are shown in FIGS. 2(a) and 2(b), being a surface contact probe and a liquid junction probe, respectively. Advantageously, the surface contact probe permits spots to be maintained in a liquid environment which is a preferred natural setting for most biological interactions. Since ES-MS introduces the sample to the mass spectrometer in a liquid solution, the possibility exists for sampling the components interacting at each point on an array while the surface array 120 remains in a liquid environment. The surface contact probe also expands the range of eluting solvents that can be used as compared to other probe designs, such as the liquid junction probe described herein. For example, the liquid junction probe generally requires a higher surface tension liquid to maintain the meniscus at the surface. No such requirement exists for the surface contact probe.

A suitable pressure differential can be used to propel fluids to the output of probe 200. For example, the input of the probe may be held at ambient pressure while a vacuum is pulled on the mode output. Alternatively, positive pressure can be used at the probe input.

A surface contact probe 200 is depicted in FIG. 2(a) in position 1 and position 2 in relation to a single surface array spot 210, position 1 being an "up" and position 2 being a "down" position. Spot 210 shown includes captured proteins 208 bound to immobilized capture proteins 206, the immobilized proteins disposed on a microarray substrate material 215, such as glass substrate. Readout is performed while probe 200 is in position 2. Following readout, probe 200 is separated (e.g., raised) from spot 210 to reach position 1, then a suitable automatic positioning device performs lateral translation to realign sampling probe 200 with another array spot. The probe 200 is again lowered into position 2 and the next spot is then sampled.

Probe 200 is preferably sized such that it has sufficiently area to completely surround an individual array spot but small enough to avoid reaching adjacent spots on the surface array. Thus, surface contact probe 200 isolates the spot being sampled from the rest of the array spots on the surface array during read out (position 2). An o-ring 222 or similar sealing device can be used to allow probe 200 to only sample a single spot during sampling, by isolating the fluid flow to a single spot.

Surface sampling probe 200 is shown as a coaxial probe, with the outer conduit 212 for flowing fluids such as reagents, wash solvents and eluting solvents from a suitable solvent delivery and switching system, such as system 115 in FIG. 1. More than two conduits can be used, such as three (3), one for a reagent, one for a wash solvent and one for an eluting solvent, with one (1) or more fluid conduits for flowing fluid from probe 200. Conduits can be in virtually any shape.

A wash solvent and then an eluting solvent are preferably applied serially onto the spot from within the sampling probe, by flowing these fluids through an outer coaxial conduit 212. In this configuration, the eluting solvent flows onto and over the array spot surface to disrupt the affinity or other binding interactions, eluting the interacting components through the inner conduit 214 of sampling probe 200 to an electrospray ion source (not shown). Electrospray ion source (not shown) is preferably interfaced with a mass spectrometer (not shown) for analyte identification.

Surface sampling probe 200 has significant advantages over other probe designs. Because the surface contact probe 200 can isolate discrete spots on the surface array from the outer environment before elution, the array readout can be performed while the surface array is in solution. This feature is generally not available for other probe designs because of mixing and dilution problems. Also, this design substantially avoids the introduction of foreign solvents into adjacent array spots while analyzing a given spot on the array.

A second probe embodiment, termed a liquid junction probe 250 is shown in FIG. 2(b). This probe 250 uses a similar positive pressure solvent delivery concept as surface contact probe 200, but contact to a spot surface 210 is a liquid bridge 255 or junction as shown in FIG. 2(b). Spot surface 210 includes captured proteins 208 bound to immobilized capture proteins 206, the immobilized proteins disposed on a microarray substrate material 215, such as glass substrate.

Like probe 200, liquid junction probe 250 is preferably sized such that it has sufficiently large (including liquid bridge 255) so that it can be positioned to surround an individual array spot but small enough to avoid reaching adjacent spots on the surface array during sampling. Balancing the flow of solvent into the probe 250 and pneumatic nebulization of the ES provides a self aspirating probe through which solvent can continuously flow if desired. Use of liquid junction robe 250 may require that the analysis be done with the array out of liquid solution because introduction of foreign solvents while analyzing one spot can affect the results obtained for the other spots by the time the other spots are analyzed. In addition, analysis in solution can dilute the eluting solvent with the solvent in which the array is immersed.

Sampling probe 250 is shown as a coaxial probe, with outer conduit 262 for flowing fluids such as reagents, wash solvents and eluting solvents from a suitable solvent delivery and switching system, such as system 115 in FIG. 1. Probe 250 includes inner conduit 264 for delivering analyte to an electrospray ion source (not shown). As with probe 200, more than two conduits can be used and conduits can be in virtually any shape. Electrospray ion source (not shown) is preferably interfaced with a mass spectrometer (not shown) for analyte identification. Following read out from one spot (e.g. an individual interaction), sampling probe 200 or 250 can be separated from the array surface and stepped under computer control (e.g., 135 and 155 in FIG. 1) to the next spot and the process repeated. At a suitable scan rate, the liquid junction can be maintained to the surface and track along with probe 200. This facilitates the reading out a thin layer chromatography (TLC) plate.

With either probe 200 or 250, the interacting proteins, wash, and interaction disruption/elution steps can each take place at a particular array spot by bringing the respective reagents to the spot sequentially through the sampling probe. For example, proteins can be first delivered for immobilization on a capture material disposed on the array, followed by a washing cycle, followed by the eluting solvent step.

Each spot could be tested more than once with the same or different interacting species. Moreover, while the analysis is easily done in a liquid environment over the chip, the analysis could take place on a "dry" array.

Referring again to FIG. 1, a mass spectrometer 150 including and electrospray interface 148 is preferably used to identify the interacting species delivered to it from the ES ion source 145. This can be accomplished on the basis of molecular mass alone or by tandem mass spectrometric analysis. Tandem mass spectrometry of whole proteins, which might be facilitated by high resolution, accurate mass determinations or by ion/ion chemistry techniques, can be used to generate sequence tags for protein identification via on-line data-based searching.

The combination of peptide identification from a proteolytic digest and subsequent protein database searching can be a powerful tool for the identification of individual proteins from complex mixtures. This is the typical procedure used for positive protein identification with MALDI-MS chip read out. However, this procedure can involve one to several hours. The approach described here provides fast (<1 s analysis time), gas-phase approaches to acquire the protein identification data.

Multiple charging of the proteins in ES-MS facilitates the dissociation of high-mass ions and allows for the determination of structural information via the analysis of the dissociation products. Thus, enzymatic digestions are not needed. Sequence-informative product ions derived from fragmentation of intact proteins can be identified in the product ion spectra that are analogous to the "sequence tags" described by Mann et al. [1], generated from the collisional activation of proteolytic digest fragments. Protein ions are almost exclusively singly charged in MALDI-MS. Therefore, the same procedures are not generally possible.

Multiple charging of the parent protein ions does complicate the tandem mass spectrometry product ion spectrum, because product ion charge states may vary from unity up to that of the parent ion. The product ion spectrum is therefore typically composed of ions of varying mass and charge. The ability to overcome this complication is provided by measurement of the mass-to-charge spacings between two or more ions. This can be done, for example, either by high resolution accurate mass capabilities like that provided with FTMS instrumentation or via ion/ion proton transfer chemistry. In the latter case, the entire product ion population is subjected to ion/ion reactions, thereby leading to a product ion spectrum where singly charged ions dominate and m/z spacing between peaks are more easily measured.

Figure 3:
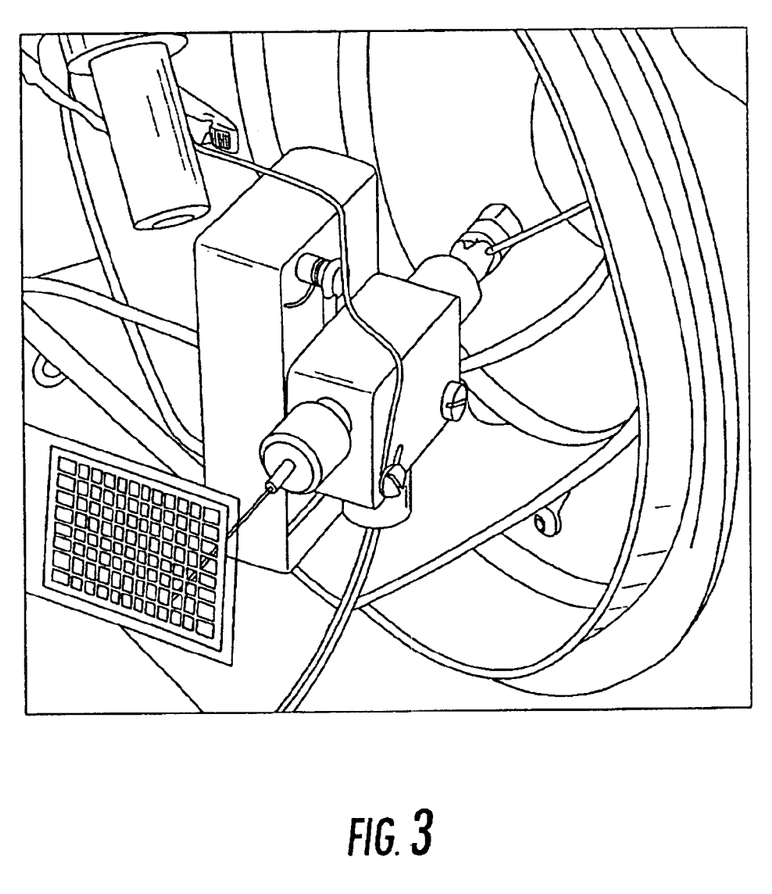
FIG. 3 illustrates a photograph of a prototype liquid junction probe and associated system for ES-MS microarray read out.

A prototype sampling probe using the liquid junction concept 250 was constructed and tested. Pictures of the actual setup are shown in FIG. 3. As proof-of-principle, the protein apomyoglobin was successfully sampled from the surface of a glass microscope slide. A sample of 0.5 pmol of the protein in solution was spotted into square areas (1 mm×1 mm) of a slide masked out by polytetrafluoroethylene grids and left to dry. The protein sampled eluted to the mass spectrometer generated a peak transient. At the end of the peak transient, the probe was lifted from the surface moved to the next spot and the elution repeated.

Figure 4:
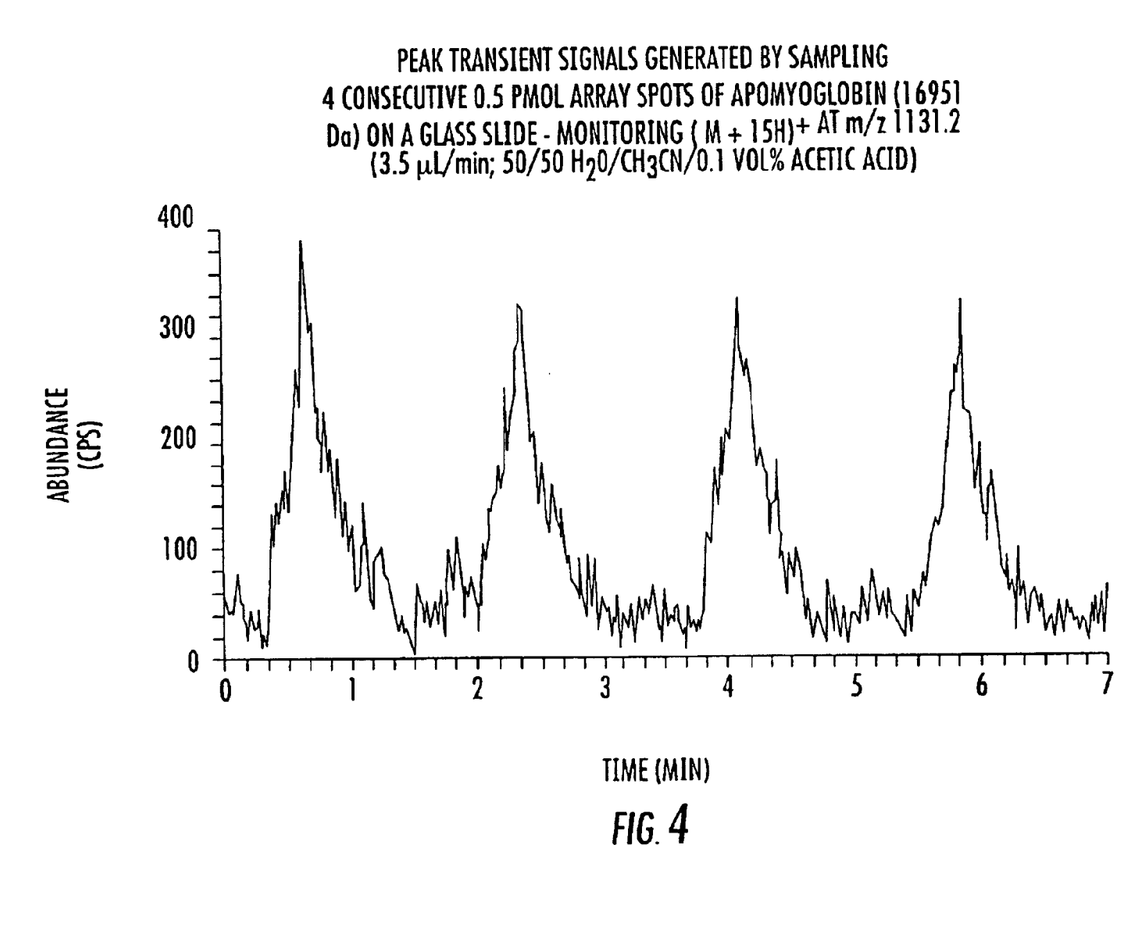
FIG. 4 illustrates peak transient signals generated by an ES-MS system using the sampling probe and system shown in FIG. 3 for 0.5 pmol per spot of apomyoglobin (16951 Da) from 4 consecutive array spots on glass slide.

FIG. 4 shows peak transients recorded for elution of the protein from 4 different spots on the slide. The signal monitored to generate this signal was that of the multiply-charged protein carrying the charge of 15 protons, i.e., $(M+15H)^+$ at m/z 1131.2.

It is anticipated that using the described system 100, read out of an individual array position will require about 30 s on a typical mass spectrometer, or about 50 minutes for a 10×10 (100 spot) chip array. This is approximately the timeframe for elution shown in FIG. 4. This read out time is relatively long compared to the theoretical time to read out an array using MALDI-MS (8.3 min or about 5 s/spot). However, when the time for the enzymatic digestion required by MALDI-MS is considered, that being one to several hours, this read out time is very competitive. The read out time will differ depending on the electric circuitry of the ES ion source. A major portion of the read out time arises from the need to elute the sample through the transfer lines from the sample surface to the mass spectrometer and to wash the lines to prevent carryover between array position analyses. Sample flow rates during read out will probably be a minimum of about 1.0 $\mu$L/min.

As an example, for the optimization of the liquid junction probe 200 shown in FIG. 2(*b*), will incorporate a 10 cm long capillary of 50 $\mu$m i.d. providing a low volume of about 0.2 $\mu$L. At 1.0 $\mu$L/min this only about 12 s to flush the volume. Several elution volumes will generally be needed to totally elute the sample and to clean the sampling capillary. Cleanup time, and thus read out time, might be lowered by increasing solvent flow rate once the proteins are eluted.

Figure 5:
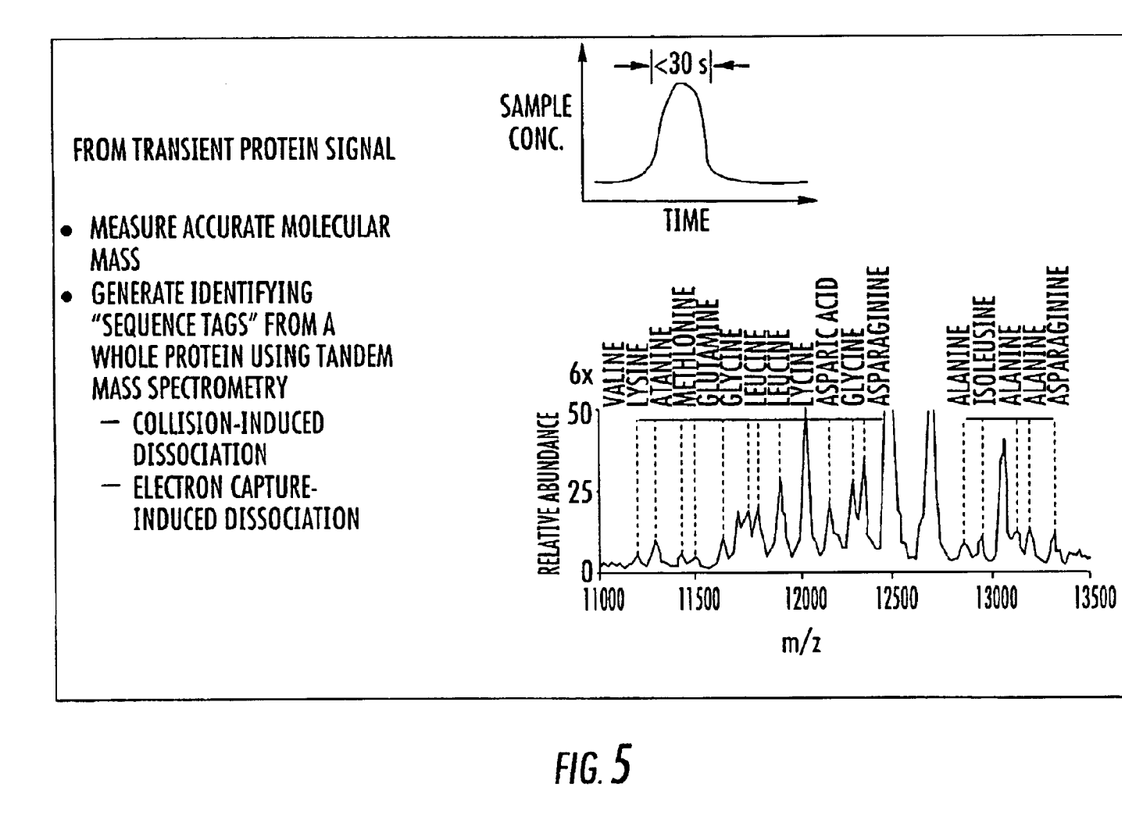
FIG. 5 illustrates a mass spectrum showing generation of a plurality of amino acid "sequence tags" from a whole protein using tandem mass spectrometry.

As noted above, in ion/ion proton transfer chemistry the entire product ion population is subjected to ion/ion reactions, producing a product ion spectrum where singly charged ions generally dominate and m/z spacing between peaks are more easily measured. Proof of the feasibility of the ion/ion proton transfer chemistry approach to protein identification has been recently reported for the identification of bacteriophage MS2 in an *Escherichia coli* lysate [2]. Using sequence tags generated via collisional activation of the multiply charged ions of the intact viral coat protein in a complex matrix (with subsequent ion/ion proton transfer reactions to produce readily interpreted singly charged product ion mass spectra), the presence of the MS2 virus could be easily detected via database searching. This is illustrated by the data in FIG. 5. As shown in FIG. 5, a plurality of resolvable sequence tags in the form of amino acid fragments having differing m/z are shown. Using the invention, this same quality of data can be obtained with a transient protein signal that can be generated from the transport of the proteins from the chip surface to the mass spectrometer.

The sampling probe/ES MS technique should be compatible with virtually any type of protein capture array, such as those employing short peptides, intact proteins or protein fragments, candidate pharmaceutical agents, DNA or antibodies. These might be obtained commercially or prepared in house using this sampling technology.

While the preferred embodiments of the invention have been illustrated and described, it will be clear that the invention is not so limited. Numerous modifications, changes, variations, substitutions and equivalents will occur to those skilled in the art without departing from the spirit and scope of the present invention as described in the claims.

REFERENCES CITED

1. Mann, M.; Wilm. M. "Error-Tolerant Identification of Peptides in Sequence Databases by Peptide Sequence Tags." Anal. Chem. 1994, 66, 4390–4399.
2. Cargile, B. J.; McLuckey, S. A.; Stephenson, Jr. J. L. "Identification of Bacteriophage MS2 Coat Protein from *E. Coli* Lysates via Ion Trap Collisional Activation of Intact Protein Ions." Anal. Chem. 2001, 73, 1277–1285.

I claim:

1. A method for identifying analytes disposed on or in surface arrays, comprising the steps of:

disposing a probe spaced apart from a first area on a surface to be sampled, wherein a liquid junction is formed between said probe and said surface;

flowing at least one eluting solvent through said spaced apart probe across said first area, wherein said solvent directs at least a portion of analyte disposed on said first area to said probe;

ionizing at least a portion of aid directed analyte into a plurality of ion fragments, analyzing said plurality of ion fragments to identify said analyte, and translating said probe across said surface to a second area, said second area different from said first area, wherein said liquid junction with said surface is maintained during said translating.

2. The method of claim 1, wherein said flowing, ionizing and analyzing steps continue during said translating step.

3. The method of claim 2, wherein said flowing, ionizing and analyzing steps continue during said automatically stepping.

4. The method of claim 3, wherein said method comprises continuously sampling.

5. The method of claim 2, wherein a positioning device is used for said automatic stepping, said positioning device providing x, y and z positional control about a substantially flat surface with at least 1 nm resolution for each of said x, y and z.

6. The method of claim 5, wherein said positioning device comprises a piezoelectric positioner and controller of a scanning probe electrochemical microscope (SECM).

7. The method of claim 1, wherein an electrospray ion source is used for said ionizing step and said analyzing step comprises mass spectrometry.

8. The method of claim 7, wherein said mass spectrometry comprises tandem mass spectrometry.

9. The method of claim 1, wherein said flowing step further comprises flowing a wash solvent before flowing said eluting solvent.

10. The method of claim 1, further comprising the step of flowing at least one reagent to said spot before flowing said eluting solvent.

11. The method of claim 1, wherein said eluting solvent and said analyte are transmitted through said probe under influence of positive pressure.

12. The method of claim 1, wherein said probe comprises a multi-axial liquid junction probe, said liquid junction probe contacting said first surface using a liquid bridge.

13. The method of claim 1, wherein said analytes comprise at least one selected from the group consisting of intact proteins, protein fragments, pharmaceutical agents and antibodies.

14. The method of claim 1, wherein said method comprises sampling spot areas of less than 0.04 $mm^2$.

15. The method of claim 1, wherein said surface array comprises at least one selected from the group consisting of a protein array, thin-layer chromotography plates, SDS polyacrylamide gel electrophoresis (SDS-PAGE), isoelectric focusing gels and affinity capture materials.

16. An automated sampling system for obtaining samples from surface arrays for analysis, comprising;
   at least one probe, said probe including an inlet for flowing at least one eluting solvent to a first area on a surface to be sampled having at least one analyte, said probe having an outlet for directing said analyte away from said first surface, wherein a liquid junction is formed between said probe and said surface, said probe providing said flowing and said directing of said analyte while spaced apart from said first area;
   an automatic positioning system for translating said probe relative to a second area, said second area different from said first area, wherein said liquid junction with said surface is maintained during said translating;
   an ion source having an input fluidicly connected to said probe for receiving said analyte and generating ions from said analyte; and
   a structure for analysis of said ions, said structure for analysis receiving said ions from said ion source, wherein said system continues to analyze said surface during said translating.

17. The system of claim 16, wherein said ion source is an electrospray ion source and said structure for analysis comprises a mass spectrometer.

18. The system of claim 16, wherein said structure for analysis comprises a tandem mass spectrometer.

19. The system of claim 16, wherein said eluting solvent and said analyte are transmitted through said probe under influence of positive pressure.

20. The system of claim 16, wherein, said probe comprises a multi-axial liquid junction probe, said probe contacting said first surface using a liquid bridge.

21. The system of claim 16, wherein said flowing of said eluting solvent and said directing said analyte away from said first surface continue while said translating of said probe.

22. The system of claim 21, wherein said system provides continuous sampling.

23. The system of claim 16, wherein said analytes comprise at least one selected from the group consisting of intact proteins, protein fragments, pharmaceutical agents and antibodies.

24. The system of claim 16, wherein said automatic positioning system provides x, y and z positional control about a substantially flat surface with at least 1 nm resolution for each of said x, y and z.

25. The system of claim 24, wherein said automatic positioning system comprises a piezoelectric positioner and controller of a scanning probe electrochemical microscope (SECM).

26. The system of claim 16, wherein said surface array comprises at least one selected from the group consisting of a protein array, thin-layer chromotography plates, SDS-PAGE, isoelectric focusing gels and affinity capture materials.

27. The system of claim 16, wherein said system provides sampling of areas of less than 0.04 $mm^2$.

28. The system of claim 16, wherein said system provides sampling of areas of less than 0.01 $mm^2$.

* * * * *